(12) United States Patent
Rose et al.

(10) Patent No.: US 6,171,548 B1
(45) Date of Patent: Jan. 9, 2001

(54) SURFACE AND AIR STERILIZATION USING ULTRAVIOLET LIGHT AND ULTRASONIC WAVES

(75) Inventors: Edward V. Rose; William E. Clark, Jr., both of Folsom, CA (US)

(73) Assignee: Spectrum Environmental Technologies, Inc., Citrus Heights, CA (US)

(*) Notice: Under 35 U.S.C. 154(b), the term of this patent shall be extended for 0 days.

(21) Appl. No.: 09/193,330

(22) Filed: Nov. 16, 1998

Related U.S. Application Data

(63) Continuation-in-part of application No. 08/999,273, filed on Dec. 29, 1997, now Pat. No. 6,090,346.

(51) Int. Cl.[7] .............................. A61L 2/10; A61L 2/025
(52) U.S. Cl. .............................. 422/20; 422/24; 422/128
(58) Field of Search .............................. 422/20, 24, 128

(56) References Cited

U.S. PATENT DOCUMENTS

| | | |
|---|---|---|
| 2,249,473 | 7/1941 | Jackson et al. . |
| 2,814,081 | 11/1957 | Stevenson . |
| 3,481,687 | 12/1969 | Fishman . |
| 4,448,750 | 5/1984 | Fuesting . |
| 5,074,322 | 12/1991 | Jaw . |
| 5,216,251 | 6/1993 | Matschke . |
| 5,330,722 | 7/1994 | Pick et al. . |
| 5,449,502 | 9/1995 | Igusa et al. . |
| 5,466,425 | 11/1995 | Adams . |
| 5,601,786 | 2/1997 | Monagan . |
| 5,658,530 | 8/1997 | Dunn . |
| 5,688,475 | 11/1997 | Duthie, Jr. . |

FOREIGN PATENT DOCUMENTS

| | | |
|---|---|---|
| 35 00 487 | 10/1986 | (DE) . |
| 0 083 448 | 7/1983 | (EP) . |
| 0 673 656 | 9/1995 | (EP) . |
| 2269275 * | 11/1975 | (FR) . |
| 2 599 255 | 12/1987 | (FR) . |
| 671922 * | 5/1952 | (GB) . |
| 2 040 150 | 8/1980 | (GB) . |
| 469009 | 9/1952 | (IT) . |
| WO 91 10455 | 8/1991 | (WO) . |

* cited by examiner

Primary Examiner—Robert J. Warden, Sr.
Assistant Examiner—Theresa T. Snider
(74) Attorney, Agent, or Firm—John P. O'Banion

(57) ABSTRACT

A method and apparatus for sterilizing organic or inorganic matter through simultaneous exposure to ultraviolet light energy and ultrasonic wave energy in a non-aqueous environment such as air. The method is suitable for use in a chamber or in a mass production assembly line setting. Purification of air is similarly accomplished using simultaneous exposure to ultraviolet light and ultrasonic energy waves.

14 Claims, 6 Drawing Sheets

SURFACE AND AIR STERILIZATION USING ULTRAVIOLET LIGHT AND ULTRASONIC WAVES

CROSS-REFERENCE TO RELATED APPLICATIONS

This application is a continuation-in-part of application Ser. No. 08/999,273 filed on Dec. 29, 1997 now U.S. Pat. No. 6,090,346.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

This invention pertains generally to sterilization methods and, more particularly, to a method and apparatus for sterilizing organic and inorganic matter in a non-aqueous environment and for sterilizing air using a simultaneous combination of ultraviolet light wave energy and ultrasonic wave energy.

2. Description of the Background Art

The effective removal of viable pathogenic microorganisms is essential to those who regularly come into contact with potentially infectious microorganisms. Medical care givers, dentists and oral hygienists are frequently exposed to bodily fluids which may contain infectious microorganisms, such as viruses, bacteria, etc. Instrumentation (including human hands) must be effectively sterilized to prevent the transmission of potentially infectious microorganisms between patients and to the workers themselves.

Microbiological researchers are constantly handling potentially infectious microorganisms as a regular part of their responsibilities and require effective and frequent sterilization of instrumentation and hands to protect themselves and their co-workers from such undesirable exposure.

People working in the field of food processing, packaging and service also have an essential need for the effective removal of potentially infectious microorganisms from a variety of food surfaces and the various equipment used in handling and processing. As part of their jobs, these workers are required to handle a variety of raw meats, poultry, seafood, baked goods, and vegetables for processing, packaging, delivery and sale to the general public. Food service workers are required to handle and prepare food products that are often to be consumed shortly thereafter by the public. Raw meats, poultry and seafood, especially, are ideal sources for the incubation and multiplication of undesired and potentially infectious microorganisms. A workers' equipment and hands must be effectively sterilized on a frequent basis to prevent infecting themselves or spreading microorganisms from a contaminated source to the rest of the supply, and thus subjecting the general public to the risk of exposure.

Similarly, there is a need for effective removal of potentially infectious microorganisms from a variety of medical and dental instruments and devices that cannot be effectively sterilized by other conventional means such as autoclaving due to their internal electronic nature. These instruments and/or devices are often used on patients where infectious microorganisms that are present on the surface of the instruments and/or devices may be transmitted onto (or even into) the patient being treated if not effectively sterilized prior to its intended use, which can cause potentially life threatening conditions.

Food products available for public consumption also require effective removal of potentially dangerous microorganisms prior to consumption by the general public. As discussed above, handling of food products by workers with non-sterilized hands can result in the spread of undesired microorganisms, or conversely, direct contact of food products with contaminated food processing and packaging equipment can also result in the spread of unwanted microorganisms.

A commonly used method for sterilizing the hands of medical, dental and food service workers is repeated washing and/or scrubbing of the hands. This procedure can be time consuming as it must be repeated frequently after the worker comes into contact with a potentially contaminated source. Also, this method may not effectively sterilize the worker's hands due to ineffective washing techniques, type of cleaning agents used, or even the length of time spent physically cleaning the hands. Constant, repetitive hand washing can also damage the skin due to use of soaps, detergents and the actual scrubbing actions that remove the skin's natural oils and can leave the skin dehydrated and irritated. The disadvantages of excessive time consumption, non-thorough hand sterilization, and skin irritation may cause the worker to avoid the frequent hand washing required to effectively prevent the spread of potentially infectious microorganisms.

Medical and dental instruments and devices are commonly sterilized via use of steam autoclaves and other methods that incorporate the use of heat, steam, gamma radiation, electron beam, and/or chemical agents to remove viable pathogenic microorganisms. However, the effectiveness of these methods varies and typically require the use of expensive, sophisticated equipment and generally involve a substantial amount of time to complete. Also, some instruments and devices are particularly sensitive to high temperatures, moisture, gamma radiation, electron beams and/or certain chemicals being used, and cannot survive these methods of sterilization. Therefore these instruments, in particular, require other methods of sterilization.

The use of ultraviolet light is another method used to sterilize organic and inorganic matter. Exposure to certain ultraviolet light band wavelengths has been discovered to be an effective means of destroying microorganisms. In using this method of sterilization, the user places the object or device to be cleaned into a chamber to expose the device or object to be cleaned to a prescribed dose of ultraviolet light. The interior of the cleaning chamber is usually coated with a reflective surface which reflects the light to ensure that all surfaces of the object being sterilized are irradiated with a sufficient amount of the ultraviolet light. The amount of time required for an adequate dosage of the ultraviolet light varies but typically requires at least ten seconds. However, the use of ultraviolet light for microbiological sterilization of organic and inorganic surface matter has historically been abandoned in favor of more sophisticated methods that employ heat, steam, gamma radiation, electron beams, and/or chemicals. This may be a result of manufacturers' desire to offer more expensive sterilization devices in lieu of simplified technology. Typically, the use of ultraviolet light has been relegated to the treatment of air and/or water, which is generally circulated past the ultraviolet light source in a cabinet or the like and then into the sterilization environment.

Other sterilization methods involve the use of ultrasonic waves which resonate through an aqueous solution in which the item to be sterilized is immersed either partially or completely. The ultrasonic waves within the aqueous solution cause zones of compression and vacuity which act physically on the object placed within the aqueous solution causing foreign substances thereon to be dislodged and dispersed within the solution. When the object to be sterilized is a human hand, for example, the aqueous solution employed must be compatible with human skin, thus limiting the types of available aqueous solutions which can be used and are effective. Furthermore, because the hands have to be immersed into an aqueous solution to utilize this sterilization method, the hands become saturated with the aqueous solution and must thereafter be dried off. The hand drying process usually entails convecting air over the skin surface for a period of time until the hands are sufficiently dry. This consumes time and may even leave the skin dehydrated. If the item to be sterilized is some other organic material, such as meats, poultry, seafood or vegetables, immersing the item into an aqueous solution can damage or even destroy its properties, thus rendering the food product useless. Similarly, certain medical instruments and devices that need sterilizing become inoperable when they are immersed in an aqueous solution. These instances illustrate the need for a sterilization method which can effectively, frequently, and quickly sterilize organic and inorganic matter in a gaseous environment.

There are also sterilization methods which combine the use of both ultraviolet light and ultrasonic waves, however in all methods until the present invention, the ultrasonic emitting step has been performed in an aqueous solution. Using this method, an ultraviolet light source is positioned to irradiate a cleaning liquid in a cleaning tank into which the item to be sterilized is immersed. A piezoelectric transducer agitates the liquid ultrasonically causing both microscopic and macroscopic agitation, which dislodges foreign substances from the surface of the item. Because the ultraviolet irradiating step occurs concurrently with the ultrasonic process, the microorganisms dislodged from the item being sterilized are subjected to ultraviolet light, thereby destroying the microorganism. In these combination methods, the disadvantages associated with each step previously mentioned still exist.

The ability to sterilize environmental air or removing germs, bacteria and the like from air is also of value to healthcare workers, industrial sites and homes, among others. The reduction of transmission of diseases, including acquired immune deficiency syndrome, by airborne carriers is done using known air purification systems. This is usually done using air filters which must be replaced at periodic interval, either alone or in combination with germicidal levels of ultraviolet radiation and many methods have been developed using this approach. Filtration means are generally placed upstream of a number of ultraviolet lamps and air is passed near the lamps.

Therefore a need exists for a method and apparatus for sterilizing organic and inorganic material in a non-aqueous environment using a combination of ultraviolet light wave energy and ultrasonic wave energy. A further need exists for an increased efficiency method to sterilize air without the complexities and expenses of methods currently employed. The present invention satisfies those needs, as well as others, and overcomes the deficiencies in prior technology.

BRIEF SUMMARY OF THE INVENTION

The present invention generally comprises a method and apparatus for sterilizing organic and inorganic materials using a combination of ultraviolet irradiation and ultrasonic emission. More particularly, the combination sterilization method of the present invention is performed in a non-aqueous environment. A typical example would be to sterilize the material while in the presence of a gas, such as air. In addition, the air itself can be sterilized. However, the material could also be sterilized in a vacuum, which those skilled in the art will appreciate is also a non-aqueous environment. It will be seen, therefore, that the invention departs from the known use of ultraviolet light and ultrasound for sterilization of materials in that the materials are not placed in a liquid, such as water, a chemical cleansing agent or the like, for sterilization. This does not mean, however, that the environment in which the materials are sterilized must be completely dehumidified in order to practice the present invention. In accordance with the invention, the materials to be sterilized are simply not immersed in a liquid. Thus the ultrasound emissions are applied in a non-aqueous environment such as air.

In accordance with an aspect of the invention, the ultraviolet light is emitted onto the surface of the material to be sterilized at wavelengths which will destroy viable pathogenic microorganisms. The material is subjected to a variable time duration sufficient to ensure complete destruction of microorganisms exposed to the ultraviolet light. During this period, the ultrasonic waves cause excitation and oscillation three-dimensionally on all exposed surfaces of the material, thereby causing microorganisms attached but not molecularly bonded to the surface of the material to become dislodged and momentarily airborne. As a result of being dislodged, the microorganisms experience a greater surface area exposure to the ultraviolet light energy than would otherwise be exposed if the microorganism were still attached to the surface of the material. The ultraviolet irradiating and ultrasonic excitation steps occur simultaneously to produce the desired effect of increased sterilization efficiency. Upon sufficient exposure time to the combined energy sources, the object is then removed from the chamber in a sterilized condition.

In accordance with another aspect of the invention, the combined use of ultraviolet light and ultrasound can be applied to mass sterilization of items produced on assembly lines. Because this sterilization method is performed in a non-aqueous environment and, hence does not require immersing the materials in a liquid, the ultraviolet light source and ultrasonic emitter assembly can be placed along the path of a moving conveyor belt. Then, as the mass produced items move along the conveyor belt, they will be exposed to the ultraviolet light from the ultraviolet light source and ultrasonic waves from the ultrasonic emitter. The ultraviolet light irradiation step occurs simultaneously with the ultrasonic wave emission process, thus making only a single exposure event necessary to produce the desired sterilization effect. This can be done without even having to stop the conveyor belt and, after exposure, the items continue along their path on the conveyor belt in a sterilized condition.

In accordance with still another aspect of the invention, mass-produced food items such as meats, poultry, seafood and vegetables can be sterilized using this combination method without affecting the taste or texture of the food items being treated. The ability of the combination sterilization method to perform effective sterilization in a non-aqueous environment such as air eliminates the need to expose the food item to any liquid which might affect the texture and/or taste of the food item. And, since the ultraviolet light impinges only on the surface of the food item being sterilized, and not beneath the surface due to its poor penetrating capabilities, the light will not "cook" or alter the interior of the food item or otherwise affect its taste or texture. It will be appreciated, however, that lengthy ultraviolet light exposure times at high power levels could cause a change in the surface characteristics of the food item being sterilized.

It will be seen, therefore, that an object of the invention is to provide a quick, efficient and reliable method for effectively eliminating potentially infectious microorganisms from environmental air using a simultaneous combination of ultraviolet light and ultrasonic waves.

Another object of the invention is to provide a combination ultraviolet and ultrasonic sterilization method in which the sterilization is performed in a non-aqueous environment such as air, a gas, air mixed with a gas, or even a vacuum.

Another object of the invention is to provide a method of sterilization which is non-hazardous and safe for the user and those in close proximity to the user.

Another object of the invention is to provide a method of sterilization which can be easily implemented to sterilize mass produced items made on an assembly line.

Another object of the invention is to provide a method of sterilization which can sterilize food items without affecting the texture and/or taste of the food item.

Another object of the invention is to provide a method of sterilization which is simple to use and which does not require special training or procedures to implement.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Referring more specifically to the drawings, for illustrative purposes the present invention is embodied in the method and apparatus generally shown in FIG. 1 through FIG. 7. It will be appreciated that the method may vary as to details of the steps and their sequence and that the apparatus may vary as to the details of its parts without departing from the basic concepts as disclosed herein.

The present invention comprises a method and apparatus for sterilizing organic and inorganic material by simultaneously exposing the material to ultraviolet light and ultrasonic waves in a non-aqueous environment, such as in air or in a vacuum, wherein the material being sterilized is not being immersed in a liquid. Hence, those skilled in the art will appreciate that the term "non-aqueous" is synonymous with "non-liquid". Unlike conventional uses of ultrasonic waves for sterilization, the present invention does not rely on a cavitation effect in a liquid in order to achieve the desired results.

Figure 1:
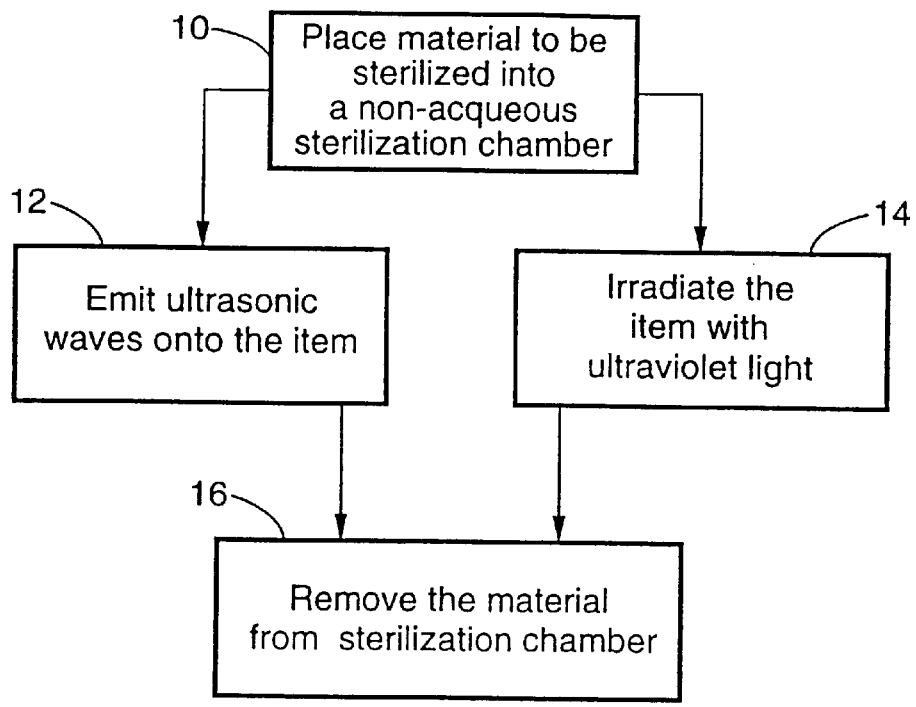
FIG. 1 is a flowchart depicting a general method to sterilize organic and inorganic material using simultaneous emission of ultrasonic waves and irradiation of ultraviolet light in accordance with the invention.

An example of the steps involved in the sterilization method of the present invention can be seen in FIG. 1. At step 10, an object or device to be sterilized is placed into an enclosed sterilization chamber which contains the path of ultraviolet light and ultrasonic waves. At steps 12 and 14, the surface of the material is simultaneously exposed to ultrasonic waves and ultraviolet light for a period of time ranging from approximately two seconds to six minutes, depending on the surface characteristics of the item being sterilized. By exposing the surface of the material to ultrasonic waves at the same time it is exposed to the ultraviolet light, the surface of the material is physically excited during irradiation by the ultraviolet light. This causes agitation and oscillation of bacteria and other undesired organisms on the surface of the material, thereby increasing the amount of surface area exposed to the ultraviolet light. By maintaining the surface of the material in a state of physical excitation while applying the ultraviolet light energy, the ultraviolet light energy will irradiate all available exposed surfaces of the material being sterilized. When sterilization is complete, the material is then removed from the sterilization chamber at step 16.

As can be seen, therefore, the present invention uses ultrasonic waves to agitate and oscillate microorganisms on the surface of the material to be sterilized, thereby increasing the surface area of the microorganism that is exposed to the ultraviolet light. This aids in the destruction of the microorganism by the ultraviolet light. In most instances, an ultraviolet irradiation period of ten seconds to one minute is sufficient, especially for bacterial sterilization. It is known that different amounts of energy in the form of microwatts are required to sterilize various microorganisms, ranging from 3,200 microwatts for common bacteria to over 400,000 microwatts; thus, sterilization for certain molds and fungi may require additional exposure time. Sterilization time may also depend on the porosity of the surface of the item being sterilized. Generally, the more porous the surface, the greater the sterilization time required. However, with food objects longer exposure times could affect the color, texture or taste of the object.

In one exemplary method, an ultrasonic emitter continuously emits ultrasonic waves while ultraviolet light is cycled on only whenever an object to be sterilized is placed within the sterilization chamber to irradiate the surface of the material being sterilized. However, it will be appreciated that during sterilization as practiced in the present invention, the ultrasonic wave emitting step 12 and the ultraviolet light irradiating step 14 must be performed in a simultaneous fashion so that the surface of the material being sterilized is exposed to ultrasonic waves sufficient to cause agitation of microorganisms.

Figure 2:
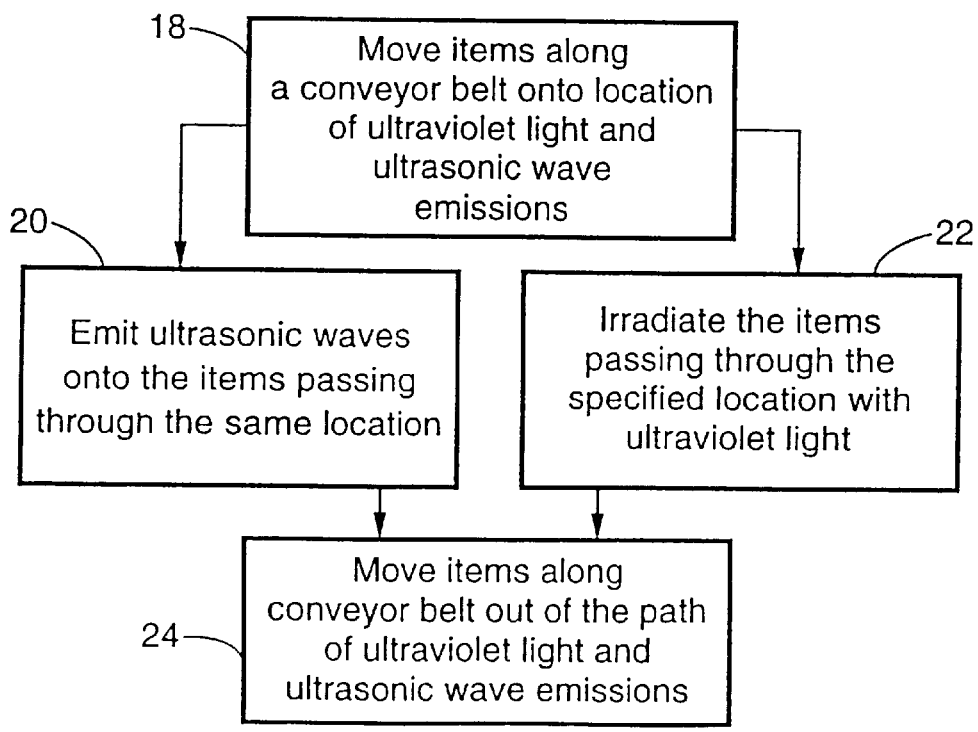
FIG. 2 is a flowchart depicting a general method to sterilize organic and inorganic material being produced on an assembly line by using simultaneous emission of ultrasonic waves and irradiation of ultraviolet light in accordance with the invention.

Referring now to FIG. 2, an example of a specific application of the sterilization method of the present invention to mass produced or bulk items using a conveyor or other transport system can be seen. Because the sterilization method of the present invention is performed in an non-aqueous environment such as air, items mass produced along an assembly line or transported along a conveyor belt or other transport device can be sterilized by simultaneously exposing the assembly line, conveyor belt or the like to ultraviolet light and ultrasonic waves such that the surface of the items moving along the conveyor belt receives at least a minimum exposure to the ultraviolet light and ultrasonic waves. For example, at step 18 the items are moved along a conveyor belt or the like into a location where the items can be exposed to ultraviolet light and ultrasonic waves. The items are then simultaneously exposed to ultrasonic waves and ultraviolet light at steps 20 and 22, respectively, and then moved out of the path of the ultrasonic waves and ultraviolet light at step 24 when exposure is complete. As indicated previously, the ultrasonic wave emitting step 20 and the ultraviolet light irradiating step 22 are performed in a simultaneous fashion so that the surface of the material is exposed to ultrasonic waves sufficient to cause agitation of microorganisms thereon and/or to produce other potentially desired effects on the surface of the item being treated.

Figure 3:
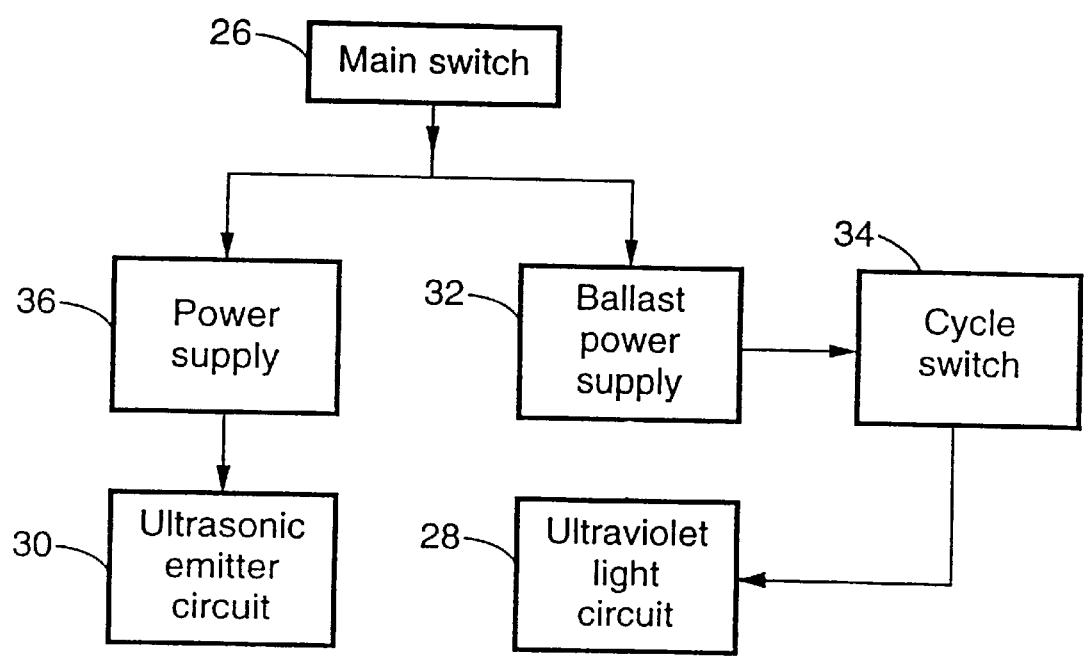
FIG. 3 is a functional block diagram of a sterilization system for carrying out the method of the invention.

Referring also to FIG. 3, a functional block diagram of a sterilization apparatus in accordance with the present invention is shown in which a main switch 26 controls an ultraviolet light circuit 28 to provide ultraviolet light for the ultraviolet irradiating steps described above and an ultrasonic emitter circuit 30 to provide ultrasonic waves for the ultrasonic emission steps described above. Ceramic piezoelectric transducers (not shown in FIG. 3.) are preferably used to emit the ultrasonic waves. Ultraviolet light circuit 28 is preferably powered by a ballast power supply 32 which may be cycled for activation and deactivation by a cycle switch 34. A conventional power supply 36 powers ultrasonic emitter circuit 30.

Figure 4:
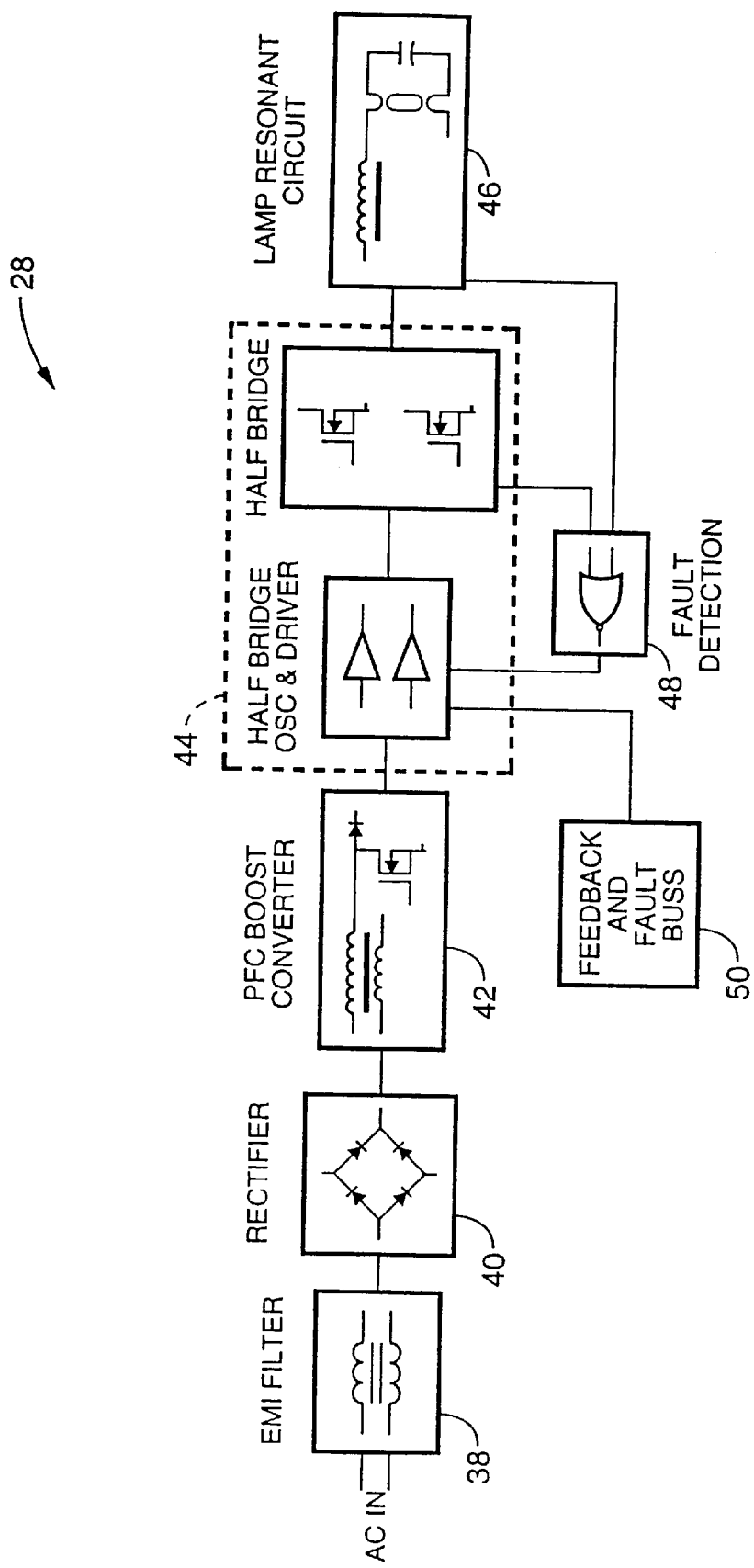
FIG. 4 is a functional block diagram of an ultraviolet light circuit of the sterilization system shown in FIG. 3.

Referring also to FIG. 4, a functional block diagram of ultraviolet light circuit 28 is shown. Ultraviolet light circuit 28 is preferably a high frequency switching supply operating in the 20 KHz to 52 KHz range, and preferably comprises an EMI filter 38, a rectifier 40, a power factor controller 42, a feedback ballast control circuit 44, an RCL series-parallel lamp resonant output circuit 46, fault detection/shutdown circuitry 48 and a feedback and fault buss 50. Power factor controller 42 is preferably a boost converter operating in critically continuous, free-running mode. Ballast control circuit 44 provides frequency modulation control of lamp resonant output circuit 46. Shutdown circuitry 48 utilizes a lamp circuit detection and comparator logic for the safe and smooth turn-off and automatic re-starting. Feedback control and lamp fault buss 50 are isolated from ballast control section 44 by opto-couplers (not shown). Those skilled in the art will appreciate that each of the foregoing elements is conventional in the art.

Ballast control section 44 preferably drives four twenty-one watt T5 type lamps (not shown) between a standby mode and a sterilization ("on") mode. In the standby mode, the circuit maintains the lamps at an approximate 10% to 20% output level. This relatively low output standby mode enhances lamp life and lowers filament temperature between sterilization cycles, but allows for virtually no heat-up time and instantaneous ionization of the lamps to full output when the circuit is switched from the standby mode to the sterilization mode. Using, for example, low pressure mercury vapor lamps such as type T5 lamps available from General Electric or other light tube manufacturers, a life cycle of up to 120,000 cycles can be expected from the lamps due to the design of the circuit as compared to 1,500 to 3,000 cycles when using conventional power supplies.

In the present invention, the ultraviolet light is typically emitted at a wavelength between approximately 180 nm and approximately 325 nm, with a wavelength of 254.7 nm having been found most effective for germicidal control, and a power density consistent with that empirically determined as sufficient to accomplish sterilization. Typical power densities range from approximately 400,000 microwatts/cm$^2$ per second to approximately 1,000,000 microwatts per cm$^2$ per second, and depend on the type of microorganism being sterilized. The ultrasonic wave energy preferably sweeps within a range of approximately 20 KHz to approximately 52 KHz in a sawtooth pattern having a cycle period of approximately 800 milliseconds per sweep. A steady 24.7 KHz transducer frequency has been found to be very effective for excitation of microorganisms on human skin, as well as for removing from the surface of the object being sterilized, all non-skinned microorganisms. The ultrasonic output from each transducer is preferably approximately 119 dB measured at a distance of 0.5 meter from the transducer with a maximum power output of approximately 7 watts using, for example, piezoelectric transducers like those available from Motorola or other ultrasonic transducer vendors.

Once activated, in a preferred embodiment the ultrasonic emission remains on continuously while the ultraviolet light is maintained in a stand-by mode and cycled to a power-on mode for sterilization using the simultaneous combination of ultraviolet and ultrasonic energy waves. The ultrasonic emission by itself does not eliminate the microorganisms on the item being sterilized; however, the ultrasonic waves cause the microorganisms to become agitated and begin to oscillate, thereby exposing more surface area of the microorganism to ultraviolet light for irradiation. In the case of air sterilization, the ultrasonic waves will cause dust particles to become excited and/or oscillate, thereby causing microorganisms on the surface of the dust particles to dislodge and become airborne so as to expose more surface area of the particles to ultraviolet light for irradiation. In addition, the ultrasound emissions can cause particles to break up, thus contorting the particles into different shapes for more effective sterilization.

Figure 5:
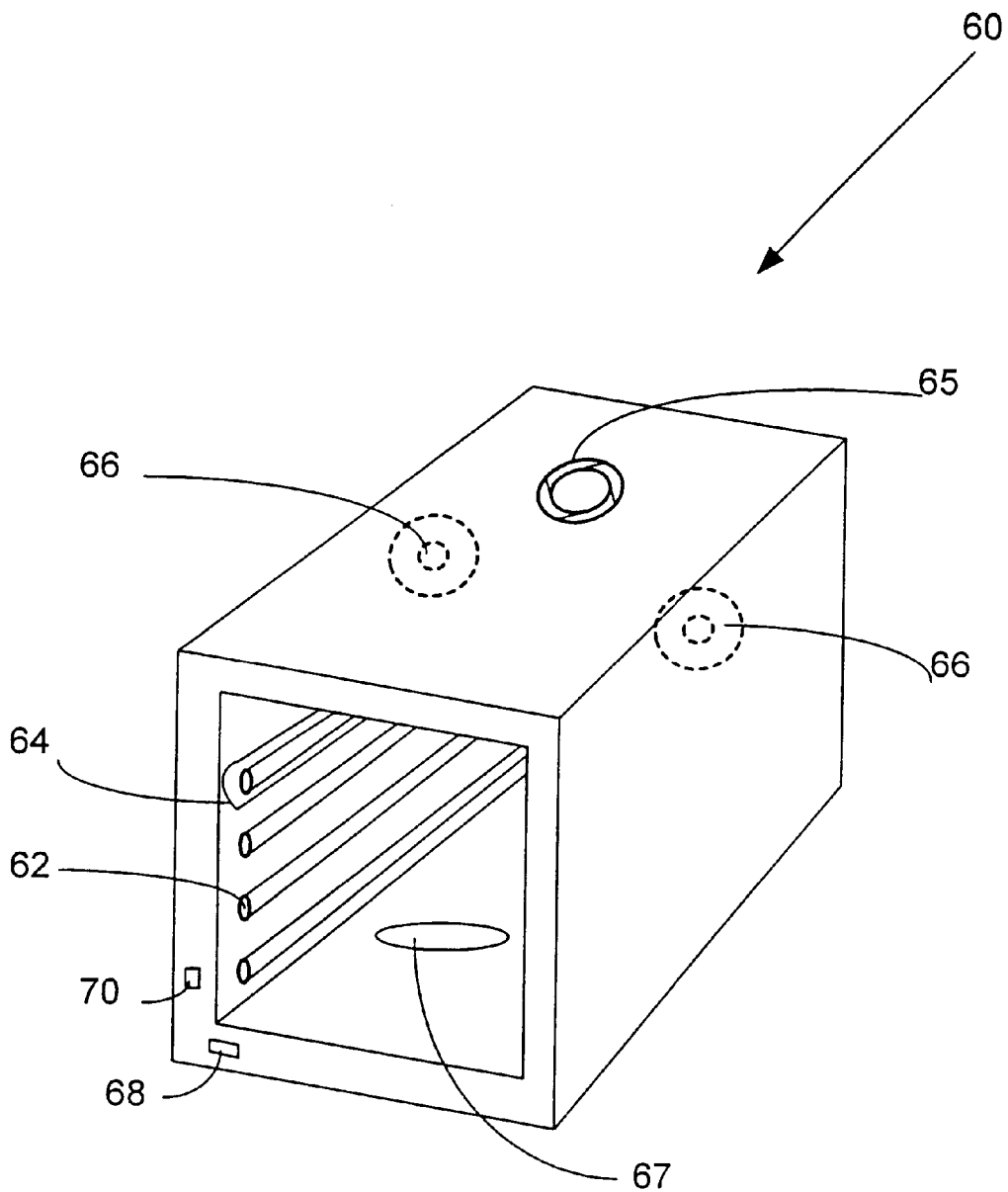
FIG. 5 is a perspective view of a sterilization chamber useful in practicing the surface sterilization method of the invention.

Referring now to FIG. 5, an embodiment of the present invention is shown as comprising a sterilization chamber 60 with approximate internal dimensions of either:
  (a) 25"×25"×25" with 4-T5 bulbs on each side wall and two transducers at the inside top middles of opposing side walls; or
  (b) 15"×15"×15" with 3-T5 bulbs on each side wall and two transducers at the inside top middles of opposing side walls; or
  (c) 10"×15"×15" with 2-T5 bulbs on each side wall and two transducers at the inside top middles of opposing side walls.

In the embodiment shown, at least one ultraviolet tube 62 such as the T5 model previously mentioned is mounted on opposing side walls and, if desired, a reflector 64 may be positioned behind tubes 62 to direct the sterilizing light wave energy generated therein toward the central portion of chamber 60. At least one source of ultrasonic wave energy 66 is mounted in chamber 60, for instance in the top middle of a side wall of chamber 60, and is aligned to provide agitating ultrasonic wave energy into the central portion of chamber 60. In a preferred embodiment, two sources of ultrasonic wave energy 66 (shown in broken lines) are mounted in chamber 60, in the inside top middle of opposing side walls of chamber 60. Objects to be sterilized may be placed directly on the bottom floor of chamber 60 or placed on a shelf therein if desired.

Chamber 60 is equipped for standard 120-volt, single-phase electrical power, has a 6" or 8" vent opening for incoming cooling air on the back (not shown), and may include single stage air-filters on the back. An exhaust fan 65 may be mounted on the top of chamber 60 to establish a cooling air stream over objects therein. A slide-out front drawer may be employed for convenience in loading objects to be sterilized and an on/off power switch is provided to manually activate the technology. The door and power switch are not shown for purposes of clarity.

On/off indicator lights 68 have a green light when chamber 60 is "on" and in the "standby" mode, and an amber or other color light (such as red) for when the unit is "on" and in the "in use" mode. A push button activates chamber 60 for frequent or repeated use so that, when the unit is in the "on" mode, sterilization can be activated by simply pushing the button. The "in use" light 68 would then come on, and the chamber 60 would be saturated with a combination of simultaneously applied ultraviolet and ultrasonic energy for a pre-determined time, depending on the object 67 being sterilized and the microorganisms of concern. The "in use" light 68 would then go out, signaling to the user that the cycle has been completed and that it was safe to open the door.

A fail-safe mechanism using a contact or vicinity switch 70 may be installed in cooperation with the door functions as a safety precaution. Structural foam on the inside walls is preferred and the exterior skins may be constructed in various metals including stainless steel, depending on the customer, and their needs/applications.

Figure 6:
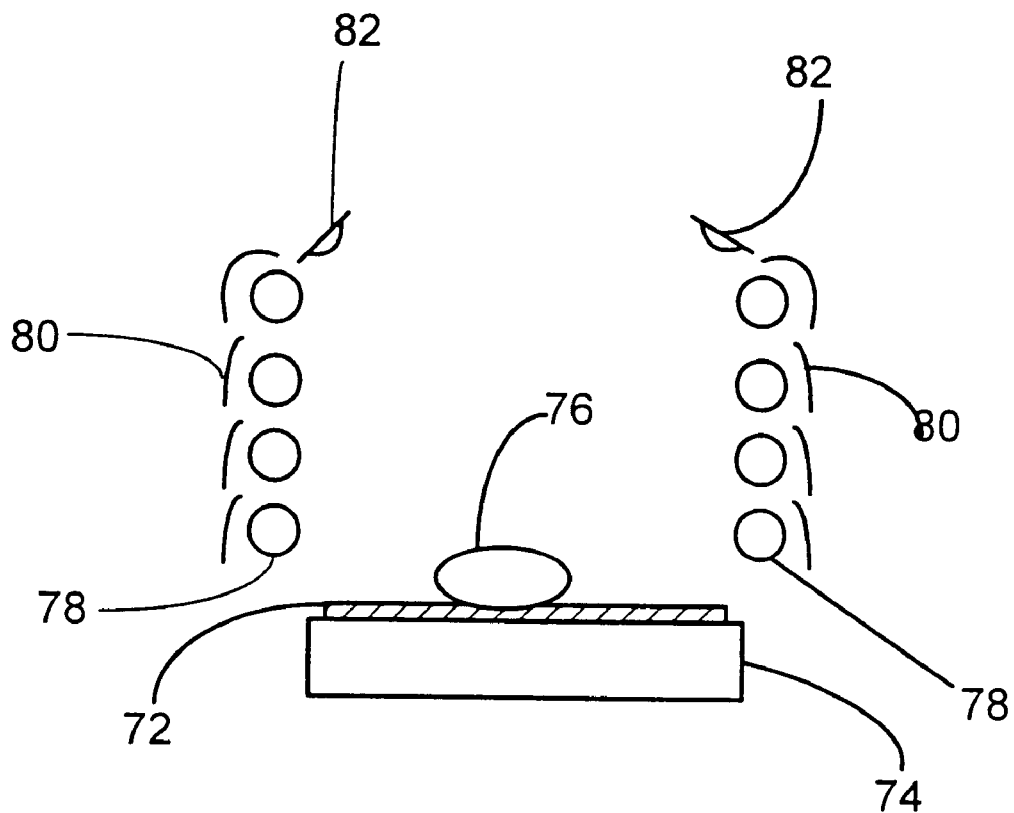
FIG. 6 is schematic illustration of a conveyor system useful in practicing the surface sterilization method of the invention.

FIG. 6 shows an in-line embodiment of the present invention comprising a conveyor belt 72 and conveyor rollers 74 suitable for moving an object 76 to be sterilized through a pair of banks of ultraviolet tubes 78 and reflectors 80. A pair of ultrasonic transducers 82 are suspended proximate the uppermost ultraviolet tubes 78 such that the ultrasonic wave energy generated thereby is directed towards the center portion of belt 72. The ultraviolet tubes 78 and reflectors 80 are similarly positioned to irradiate belt 72 with ultraviolet light and ultrasonic energy waves. Sterilization of the object 76 is accomplished using simultaneous exposure to ultraviolet light and ultrasonic energy waves. If the dimensions of the belt 72 and the bank of ultraviolet tubes 78 is is about 25 inches by 25 inches, sterilization may be accomplished using ultrasonic transducers 82 and ultraviolet tubes 78 similar to those shown in FIG. 5 and described previously.

Figure 7:
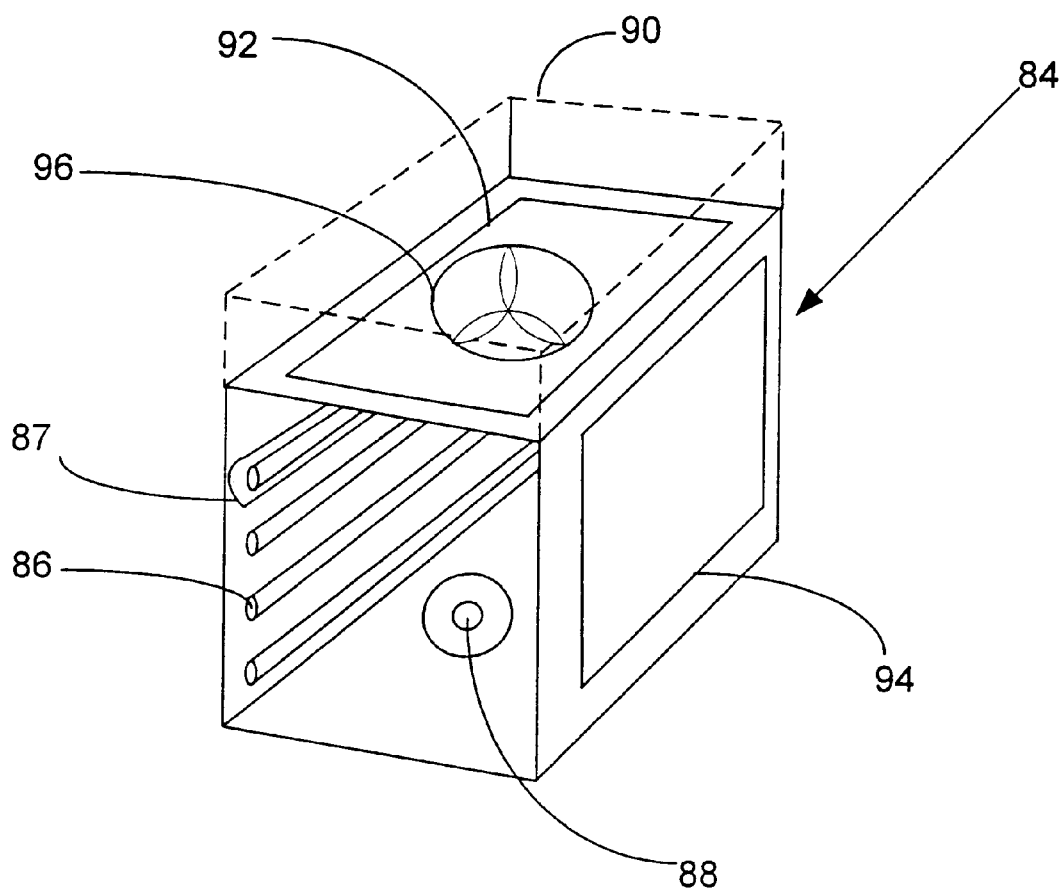
FIG. 7 is perspective schematic in part of a sterilization chamber useful in practicing the air sterilization method of the invention in a stand-alone mode or in association with a larger air handling system.

FIG. 7 illustrates an exemplary air sterilization unit 84 using sources of ultraviolet wave energy 86 and ultrasonic wave energy 88 as a means for sterilization of a body or stream of air by simultaneous activation of the sources of ultraviolet wave energy 86 and ultrasonic wave energy 88 of the present invention. Air sterilization unit 84 is representative of an upright floor-standing style and typically sized for 150 cfm, 250 cfm, 450 cfm, and 600 cfm rated capacities, although larger units may be custom designed using the same overall design concept. Typically, the 150 cfm and 250 cfm units have four T5 type ultraviolet light sources 86 and one ultrasonic transducer 88, while the 450 cfm and 600 cfm units may have as many as eight T5 ultraviolet light sources 86 and one or two ultrasonic transducers 88. Reflectors 87 may be included to direct ultraviolet radiation towards the central portion of chamber 84. Although the light tube sources of ultraviolet wave energy 86 are shown mounted on the side wall of chamber 84, it should be appreciated that mounting the tubes 86 in the interior portion of chamber 84 is also an effective positioning as air streams may then flow over the tubes 84.

Sterilization chamber 84 contains a commercially available air filter section 90 (shown in broken lines for purposes of clarity), typically comprising gauze, charcoal or HEPA filters, alone or in combination. Air inlet port 92 and outlet port 94 are capable of incorporating either grills or ducted connections depending on the placement and application and are useful in testing described hereinafter. A fan 96 is located in either the inlet port 92 or outlet port 94 to move an air stream to be sterilized through the sterilization chamber 84. An acoustical blanket, insulating foam, or other sound deadening measures to cut down on noise emissions, may be added.

It should be appreciated that the sterilization chamber 84 may be used in conjunction with a conventional HVAC air handling system within a residence, hospital, industrial operation or the like in which a stream of air moves through chamber 84 once and then into the area of use. It should also be appreciated that the sterilization chamber 84 may be used in a stand-alone operation for instance in a residence or office or hospital emergency room in which room air is recirculated through the sterilization chamber 84 using ports 92 and 94.

EXAMPLE 1

Surface Sterilization

The purpose of the testing reported herein is to demonstrate the sterilization efficacy of the present inventive simultaneous application of ultraviolet light wave energy and ultrasonic sound wave energy on selected groups of microorganisms including viruses, bacteria, fungi, molds and other unwanted surface and airborne biological contaminants on both solid surfaces and air streams.

(a) Evaluation of Surface Sterilization Using Simultaneous Application of Ultraviolet Light Wave Energy and Ultrasonic Wave Energy Testing was performed over a period of 24 months to provide a variety of working conditions and environments to allow for monitoring of any increased or decreased effectiveness based upon the use of the present inventive simultaneous application of ultraviolet light wave energy and ultrasonic sound wave energy. Conditions were selected that could provide a wide range of temperatures, humidity, air turbulence, natural and artificial light, and other hostile working parameters. Environments were chosen that offered a variety of known and/or suspected surface and airborne pathogen types that could be monitored to evaluate the efficacy of the technology throughout the course of the study.

(b) Preparation of Test Organism Dilutions of Colony-Forming Units

In order to assess the microbiological sterilization efficacy of the present inventive simultaneous application of ultraviolet light wave energy and ultrasonic sound wave energy for sterilization, a variety of product surfaces were challenged with test organism dilutions of various inocula of colony-forming units per milliliter (CFU/ml). The primary sterilization challenge rests with utilizing an extremely large load of inoculum (significantly more than what might normally be encountered on the product surface) as well as using normally encountered levels of inocula in order to assess the procedures efficacy at these levels. The result is that the present invention has a remarkable and unexpected high antimicrobial efficacy at differing microbial levels.

Challenge organisms consisted of *Salmonella choleraesuis*, ATCC 14028, and *Escherichia coli*, ATCC 8739, grown on Tryptic Soy Agar (TSA) with 5% sheep blood and MacConkey (MAC) agars. Preparatory to the test, a grown stock culture of each of the specified microorganisms was inoculated to the surface of the above agars. Agars were incubated at 35 C+/−2 C for 72 hour increments. Subsequent growth was assessed for purity and colony morphology. Smooth colony types were harvested by use of a sterile wooden applicator stick and suspended in sterile (0.85%) saline, adjusting the suspension equivalent to a MacFarland Standard 1.0. This approximates $3.0 \times 10^8$ cells/ml (300,000,000 cells/ml).

Following preparation of the microorganisms, ten-fold dilutions were prepared using a 1 ml amount of the previously described suspension and a 9 ml amount of diluent (sterile 0.85% saline). Subsequent ten-fold serial dilutions were prepared in a likewise manner. The number of colony forming units per milliliter in each suspension was determined. This value served to determine the size of the inoculum to use in the test. The suspensions were evaluated by use of the plate count agar method to establish an approximate suspension density of microorganisms.

The suspension matching that of a MacFarland Standard 1 was used as the primary sterilization to the product as well as other suspensions most closely matching 100–300 CFU/ml and <100 CFU/ml as extrapolated from previous plate count agar studies. All tests were performed in triplicate. Product test templates were prepared on the product surface by outlining the surface contact plate area (approximating 25 cm$^2$) by using a wax pencil. From each test suspension, a 0.5 ml volume was applied to the product test templates in a format representing (in triplicate) "before" and "after". The inoculum was allowed to dry for 10–15 minutes. Surface Contact Plates(SCP) [D/E Neutralizing Agar] were used for testing the product test surface.

Upon completion of drying, the SCP were applied onto the "before" product test sites, pressed lightly, removed and covered with its lid. The SCP were pressed and not wiped on the product test surface to prevent abnormal distribution of CFU's on the surface. The "after" product test sites were processed in the normal Micro-Clean sterilization procedure as established by Spectrum protocols. Upon completion of this procedure, SCP were applied to the "after" product test sites as previously discussed. Following this sampling, the SCP were labeled, secured with tape, refrigerated and transported to the testing laboratory for analysis.

The SCP were incubated at 35 C+/−2 C for 72 hours. SCP were observed at 24, 48 and 72 hour intervals and evaluated for CFU's to be recorded as actual CFU (if countable) or as >100 CFU (reflecting Too Numerous To Count CFU). CFU results are expressed as an average of the triplicate testing. Molds are reported as observed CFU's. No distinction between bacteria and yeast was attempted and no identification of any CFU was done. It should be recognized that the purpose of this sterilization challenge is to assess the effectiveness of the present invention as to its anti-microbial efficacy on the product surface.

(c) Surface Sterilization Testing

The simultaneous application of ultraviolet light wave energy and ultrasonic sound wave energy as a method of sterilization of the present invention was evaluated for efficacy as a stand alone process, in combination with the use of both standard and HEPA filters for performance on airborne microorganisms (bioaerosols), and in a variety of liquids for possible aqueous applications. Testing was performed using multiple time exposures to ascertain the efficacy of the invention on the varying surface types throughout the course of the study. Standard time sequences of 5, 10, 15, 30, 45, and 60 second exposures were established prior to the start of the test study to evaluate and compare any changes in the effectiveness of the technology on the surface types selected and tested.

During the course of the test study, over 3,500 samples were randomly collected and analyzed by independent test organizations from over 100,000 items processed using the simultaneous application of ultraviolet light wave energy and ultrasonic sound wave energy. The estimated value of the items treated and sampled during the course of this study has been placed in excess of $500 mm. The validation test results on the use of the present invention are summarized below.

Surface types selected for testing included a variety of plastics, glass, metals, woods, paper, laminates, concrete, and foods with varying textures and surface conditions. Of the selected surface types tested, differentiation in the range of textures, shapes, densities, and uniformity was continuously reviewed to ensure that sufficient quantity of each was represented within the overall test study. And finally, media surface types selected for the study were chosen for their ability to absorb, adsorb, collect, alter, bond, and otherwise affect the various types of microorganisms that were the validation criteria for the testing.

(d) Test Using Normal Levels of Microorganisms

Table 1 shows the results of microbial measurements on a variety of samples collected via use of: Tryptic Soy Agar (with panase); Rose Bengal Agar; Mannitol Salt Agar; MacConkey Agar; and/or sterile blank contact plates. All samples were incubated at 28–35° C. upon delivery to the analytical testing facility. Samples were analyzed for the presence of CFU's at 24 and 48 hour intervals (unless longer incubation times were required for specific agar types) after collection and preparation of the contact plates. Sample collection and analyses were performed by certified and professionally licensed microbiologists.

Table 2 shows the results of tests for the presence of microorganisms after the various test objects to be cleaned were sterilized in sterilization chamber 60 using the present inventive simultaneous application of ultraviolet light wave energy and ultrasonic sound wave energy in an air environment. It can be seen that within the range of measurement errors, the sterilization was nearly 100% effective.

(e) Test Using High Levels of Microorganisms

Surfaces were inoculated with microbiological suspensions consisting of one or more of the following: saline solution with Penicillium mold species; *E. Coli* bacteria (ATCC 25923); *Staphylococcus epidermidis* bacteria (ATCC 12228); and aspergillius flavis mold. Inoculum preparation and applications were administered by trained laboratory personnel in on-site settings under the supervision of professionally licensed and certified microbiologists.

Table 3 shows a summary of analytical test results collected from inoculated surface samples prior to sterilization using the present invention. Reported concentrations represent the number of CFU's present in a 25 cm-sq. area. Thirty-five percent of the samples collected were from inoculated surfaces allowed to dry. Surface samples were collected via use of: Tryptic Soy Agar (with panase), Rose Bengal Agar, Mannitol Salt Agar, MacConkey Agar and/or sterile blank contact plates. All samples were incubated at 28–35° C. upon delivery to the analytical testing facility.

Samples were then sterilized in sterilization chamber 60 using the present inventive simultaneous application of ultraviolet light wave energy and ultrasonic sound wave energy in an air environment. The sterilized test objects were then analyzed for the presence of CFU's at 24 and 48 hour intervals (unless longer incubation times were required for specific agar types) after collection and preparation of the contact plates. Certified and professionally licensed microbiologists performed sample collection and analyses. It can be seen that within the range of measurement errors, under extremely "infected" conditions, the sterilization was nearly 100% effective. Test results are shown in Table 4.

(f) Surface Sterilization Test Conclusions

Results of the twenty four month test study conducted on the use the present inventive simultaneous application of ultraviolet light wave energy and ultrasonic sound wave energy on a variety of surface types in a range of conditions and environments has validated that the present invention is an effective means of biological decontamination for exposed surfaces based upon the overall percent reduction of viable pathogenic microorganisms on a sufficient number of random test samples collected and analyzed.

The above study confirmed that surfaces exposed to the simultaneous application of ultraviolet light wave energy and ultrasonic sound wave energy in an air environment showed a consistent reduction in quantifiable microorganisms in excess of 99.99 percent, compatible with or clearly exceeding other approved methods of surface sterilization currently available. Test results obtained from over 1,875 samples of surfaces exposed to the inventive sterilization process showed no signs or symptoms of damage, fatigue, or discoloration as a result of exposure to the technology. In numerous samples tested, repeated exposures to the sterilization process were conducted to ascertain the failure rate from repeated long-term exposure. No samples were identified that revealed visible or other noticeable signs of damage, failure or distress.

Those skilled in the art will appreciate that the invention as described can be implemented using conventional circuitry and that the invention can vary as to configuration and design, including use of analog and digital equivalents for circuit elements. It will also be appreciated that, except as described herein, circuitry to emit ultrasonic waves and ultraviolet light is commercially available and, therefore, is not described in detail herein and does not form a part of the invention as claimed. Accordingly, the present invention provides for the sterilization of objects using a combination of simultaneously applied ultraviolet light and ultrasonic waves in a non-aqueous environment such as air. The simultaneous emission of ultrasound and ultraviolet light complement each other and can effectively sterilize either organic or inorganic items in a gaseous environment. This simultaneous combination of ultraviolet light and ultrasonic waves provides for effective sterilization of items without having to place the item in a water or other liquid solution during exposure to the ultrasonic waves. The present invention also provides for the sterilization of a stream or body of air using a combination of simultaneously applied ultraviolet light and ultrasonic waves. Although the description above contains many specificities, these should not be construed as limiting the scope of the invention but as merely providing illustrations of some of the presently preferred embodiments of this invention. Thus the scope of this invention should be determined by the appended claims and their legal equivalents.

TABLE 1

Analytical Test Results Collected from
Randomly Selected Untreated Surface Samples
Prior to Sterilization Using The Present Invention

| Surface Media | Number of Samples | Range of CFU's Present |
|---|---|---|
| Plastics | 410 | 13– TNTC* |
| Glass | 65 | 7– 95 |
| Metals | 185 | 4– 89 |
| Woods | 45 | 11– TNTC* |
| Paper | 95 | 2– 97 |
| Laminates | 320 | 8– 90 |
| Concrete | 60 | 1– 74 |
| Foods | 375 | 3– TNTC* |
| Total Number of Samples | 1,555 | |

*TNTC = Too numerous to count (>100 CFU's/100cm-sq)

TABLE 2

Summary of Analytical Test Results
Collected from Surface Samples After Application
of Simultaneous Ultraviolet and Ultrasonic Energy

| Surface Media | Number of Samples | Range of CFU's Present |
|---|---|---|
| Plastics | 410 | 0* |
| Glass | 65 | 0* |
| Metals | 185 | 0* |
| Woods | 45 | 0–2+** |
| Paper | 95 | 0* |
| Laminates | 320 | 0* |
| Concrete | 60 | 0–2+** |
| Foods | 375 | 0–2+** |
| Total Number of Samples | 1,555 | |

*Zero (0) CFU's denotes no microbial growth present (terminal sterility)
**0–2 CFU's present denotes statistical margin of error allowed for during sample collection and handling by on-site laboratory personnel.
2+denotes the presence of microbial growth 72 hours after completion of treatment application.

TABLE 3

Summary of Analytical Test Results
Collected from Inoculated Surface Samples Prior to
Sterilization Using the Present Invention

| Surface Media | Number of Samples | Range of CFU's Present |
|---|---|---|
| Plastics | 58 | 15,000–150MM* |
| Glass | 27 | 15,000–50MM* |
| Metals | 41 | 150,000–50MM* |
| Woods | 25 | 100,000–10MM* |
| Paper | 18 | 100,000–10MM* |
| Laminates | 52 | 1.5–10MM* |
| Concrete | 10 | 50,000–1MM* |
| Foods | 89 | 10,000–10MM* |
| Total Number of Samples | 320 | |

*MM = million

TABLE 4

Summary of Analytical Test Results Collected from Inoculated Surface Samples After Sterilization Using the Present Invention

| Surface Media | Number of Samples | Range of CFU's Present |
|---|---|---|
| Plastics | 58 | 0* |
| Glass | 27 | 0* |
| Metals | 41 | 0* |
| Woods | 25 | 0–2+** |
| Paper | 18 | 0* |
| Laminates | 52 | 0* |
| Concrete | 10 | 0–2+** |
| Foods | 89 | 0–2+** |
| Total Number of Samples | 320 | |

*Zero (0) CFU's denotes no microbial growth present (terminal sterility)
**0–2 CFU's present denotes statistical margin of error allowed for during sample collection and handling by on-site laboratory personnel.
2+denotes the presence of microbial growth 72 hours after completion of treatment application.

What is claimed is:

1. A method for sterilization of an organic or inorganic object, comprising the steps of:

(a) exposing an object to ultrasonic waves in a non-liquid environment to cause excitation and oscillation of exposed surface areas of the object and to cause a microorganism attached to the object to become dislodged from the object and airborne; and (b) simultaneous with said step of exposing said object to ultrasonic waves, exposing said airborne microorganism to ultraviolet light, wherein said airborne microorganism experiences a greater surface area exposure to said ultraviolet light than it would experience if still attached to the surface of the object;

(c) wherein said simultaneous exposure to said ultraviolet light and said ultrasonic waves effects sterilization of said object.

2. A method as recited in claim 1, wherein said non-liquid environment comprises air.

3. A method as recited in claim 1, wherein said ultraviolet light is at a wavelength from approximately 180 nanometers to approximately 325 nanometers.

4. A method as recited in claim 1, wherein said ultrasonic waves are at a sweep frequency between approximately 20 KHz and approximately 52 KHz.

5. A method as recited in claim 1, wherein the sterilization is accomplished in a chamber.

6. A method as recited in claim 1, wherein the sterilization is accomplished on a conveyor belt.

7. A method as recited in claim 1, wherein said ultraviolet light is at a wavelength of approximately 250 to 260 nanometers for germicidal sterilization.

8. A method as recited in claim 1, wherein said ultrasonic waves are at a frequency of approximately 24 to 25 KHz for excitation of certain microorganisms.

9. An apparatus for sterilization of an organic or inorganic object, comprising:

(a) an ultrasound source configured to (i) cause excitation and oscillation of exposed surface areas of the object in a non-liquid environment, and (ii) cause a microorganism attached to the object to become dislodged from the object and airborne; and (b) an ultraviolet light source configured to expose said microorganism to ultraviolet light simultaneously with exposure of said object to said ultrasonic waves, wherein said airborne microorganism experiences a greater surface area exposure to said ultraviolet light than it would experience if still attached to the surface of the object;

(c) wherein said simultaneous exposure to said ultraviolet light and said ultrasonic waves effects sterilization of said object.

10. An apparatus as recited in claim 9, wherein said non-liquid environment comprises air.

11. An apparatus as recited in claim 9, wherein said ultraviolet light source emits ultraviolet light at a wavelength from approximately 180 nanometers to approximately 325 nanometers.

12. An apparatus as recited in claim 9, wherein said ultrasound source emits ultrasonic waves at a sweep frequency between approximately 20 KHz and approximately 52 KHz.

13. An apparatus as recited in claim 9, wherein said ultraviolet light source and said ultrasound source are positioned within a chamber.

14. An apparatus as recited in claim 9, wherein said ultraviolet light source and said ultrasound source are positioned adjacent to a conveyor belt.

* * * * *